US005753496A

United States Patent [19]

Morikawa et al.

[11] Patent Number: 5,753,496

[45] Date of Patent: May 19, 1998

[54] APPARATUS FOR INTRODUCING BIOLOGICAL SUBSTANCES OR BIOLOGICALLY ACTIVE SUBSTANCES

[75] Inventors: Hiromichi Morikawa, Hiroshima; Akira Kijihana, Nara, both of Japan

[73] Assignee: Nippon Medical & Chemical Instruments Co., Ltd., Osaka, Japan

[21] Appl. No.: 758,332

[22] Filed: Dec. 3, 1996

[30] Foreign Application Priority Data

Dec. 5, 1995 [JP] Japan .................................... 7-316608

[51] Int. Cl.$^6$ ...................................................... C12M 3/00

[52] U.S. Cl. ........................................... 435/285.3; 935/85

[58] Field of Search .............................. 435/285.3, 283.1, 435/285.1; 935/85

[56] References Cited

U.S. PATENT DOCUMENTS 5,179,022 1/1993 Sanford et al. ......................... 435/287
5,478,744 12/1995 Sanford et al. ...................... 435/285.1

FOREIGN PATENT DOCUMENTS

B-58061 1/1991 Australia ....................... C12N 15/87
405 696 A 2/1990 European Pat. Off. ........ C12N 15/87
5508316 11/1993 Japan ............................ C12N 15/00

OTHER PUBLICATIONS

Appl. Microbiol. Biotechnol. (1989) 31:320–322, 1989.

*Primary Examiner*—David A. Redding
*Attorney, Agent, or Firm*—Fulbright & Jaworski L.L.P.

[57] ABSTRACT

An apparatus for injecting biological substances or biologically active substances into biological materials without contaminating or damaging the biological materials, which includes a sealed cylinder at one end of which is connected a source of compressed fluid, a vibration plate attached to the other end of the cylinder, a hammer bullet provided in the cylinder, a flow path provided between the source of compressed fluid and the cylinder and a valve provided within the flow path, wherein the biological substances or biologically active substances are retained on the face of the vibration plate opposite the hammer bullet and is made to radiate from the vibration plate and to the biological material by opening the valve and applying a moving force to the hammer bullet, which, in turn, strikes the vibration plate.

46 Claims, 13 Drawing Sheets

APPARATUS FOR INTRODUCING BIOLOGICAL SUBSTANCES OR BIOLOGICALLY ACTIVE SUBSTANCES

FIELD OF THE INVENTION

The present invention relates to an apparatus for introducing biological substances or biologically active substances, such as DNA or chromosomes, into biological material or biological cells.

BACKGROUND OF INVENTION

An apparatus for introducing biological substances or biologically active substances into biological material, like biological tissues or biological cells, is disclosed, for example, in Japan Laid-Open Patent Publication HEI 5-508316. The apparatus is shown in FIG. 23 to 27 and comprises a high-pressure gas supply system 30, an impacting mechanism 31 having a rod 32, a high-pressure chamber 33, a first membrane 34 for generating an instantaneous shock wave from the high-pressure gas source, a housing 35 for releasing, receiving and ventilating the shock wave, a throat area 37 having a second membrane 36 which enables compatible insertion and which can convert the shock wave of gas generated by the impacting mechanism 31 into acceleration energy for micro-bullets, and a nozzle 38 connected so as to aim at various types of biological targets (biological materials) 8. The nozzle can be easily interchanged with other nozzle constructions. The apparatus also includes a source of pressure fluid 6, an electrically accelerating mechanism 40 to accelerate the rod 32 to penetrate the first membrane 34 and a vacuum means 41 for evacuating the inside of the housing 35.

In this apparatus, a compressed inert gas (200 kg/cm$^2$ or so), like helium, is used as a pressure source. A shock wave resulting from use of this compressed gas (compressed fluid **6*a*) is released outside by making a small hole on the first membrane 34 from inside of the high-pressure chamber 33 by using a sharp tip of the rod 32, thereby instantaneously introducing the gas into the throat area 37 as shown in FIG. 24 to 26. The introduced gas stream impacts the rear face of the second membrane 36, composed of polyimide or polyester, which is attached opposite to the biological material 8 in the throat area 37 and which retains a mixture of (1) biological substances 7, like DNA, or biologically active substances 7', and (2) fine particles of gold or tungsten having a diameter of approximately 1 μm (usually referred to as a carrier). The mixture attached to the second membrane 36 is propelled into the biological material 8 when the membrane is struck by the shock wave generated as described above. In this method, however, there is a problem in that the second membrane 36 is crushed by the high pressure of the compressed fluid 6*a* generated when the second membrane 36 receives the shock wave impact, and the debris and a jet of the gas (compressed fluid) spout in the direction of and against the biological materials 8, thus colliding with the biological material 8 into which the biological substance 7 or biologically active substance 7' is introduced. As a result, the biological materials 8** is contaminated or otherwise damaged.

For the purpose of solving the aforementioned problems, a different apparatus was devised in which the second membrane 36 is inserted into the upper portion of the throat area 37, as shown in FIG. 27, and a screen 39 is provided close to the second membrane 36 between the second membrane 36 and biological material 8. This construction allows radiation of only the biological substance 7 or biologically active substance 7' without causing the second membrane 36 to burst during expansion. However, in this conventional injection apparatus provided with a screen, problems result, which include the fact that the passing ratio of the biological substances or biologically active substances decreases and the pressure for introducing the biological substances or biologically active substances is reduced.

SUMMARY OF INVENTION

It is, therefore, an object of the present invention to solve the problems in the conventional injection apparatus described above.

More specifically, it is an object of the present invention to provide a more compact injection apparatus.

Yet another object of the present invention is to provide an injection apparatus that provides a sufficient amount of introduction pressure even when the pressure of the compressed fluid for shooting the biological substances or biologically active substances is low.

Still another object of the present invention is to provide an injection apparatus which does not result in the crushing of the membrane retaining the biological substances or biologically active substances.

Additionally, an object of the present invention is to provide an injection apparatus, as described above, which prevents the biological materials into which biological substances or biologically active substances are introduced from being contaminated or damaged by the compressed fluid or debris of the membrane.

A further object of the present invention is to provide an injection apparatus that eliminates the pressure loss for introducing into the biological material.

In accordance with one embodiment of the present invention and for purposes of attaining the aforementioned objects, the present invention provides an apparatus for introducing biological substances or biologically active substances having a sealed cylinder, a compressed fluid source connected to one end of the cylinder, a vibration plate attached to the other end of this cylinder, a hammer bullet provided in the cylinder, a flow path provided between the source of compressed fluid and the cylinder and a valve provided within this flow path, wherein when the valve is opened, the compressed gas moves the hammer bullet into contact with the vibration plate and causes biological substances or biologically active substances retained on the face of the vibration plate opposite the face contacted by the hammer bullet to radiate from the vibration plate.

In a further and preferred embodiment of the invention, the apparatus includes a case for mounting the sealed cylinder.

Preferably, the compressed fluid is an inert gas, air, water, or a variety of oils. Alternatively, explosives may be placed onto the rear face of the hammer bullet and exploded to drive the bullet toward and into contact with the vibration plate.

Furthermore, the present invention preferably includes apertures in the sidewalls of either end of the cylinder for exhausting from the cylinder the fluid upon contact of the hammer bullet. In the embodiment, in which a case is provided, the case includes ducts for exhausting the fluid. Preferably, the ducts have vacuum means to evacuate the inside of the case, as necessary.

According to another embodiment of the present invention, there is provided an apparatus for introducing biological substances or biologically active substances having a cylinder, a hammer bullet provided in the cylinder, a driving means provided at one end of the cylinder for moving the bullet and a vibration plate attached to the other end of the cylinder, wherein the driving means moves the hammer bullet into contact with the vibration plate and causes the biological substances or biologically active substances retained on the face of the vibration plate opposite the face contacted by the hammer bullet to radiate from the vibration plate. Advantageously, the apparatus includes a case for mounting the sealed cylinder.

Preferably, the impact pressure of the hammer bullet is about 1 to 30 $kg/cm^2$.

Additionally, the apparatus may include a stopper for stopping the hammer bullet at a predetermined position when it contacts the vibration plate.

According to one design, the vibration plate is a flat plate and the face of the hammer bullet opposite is formed to fit the flat face of the vibration plate.

According to one embodiment, the vibration plate consists of a titanium alloy. According to another embodiment, the vibration plate is composed of a layer of a titanium alloy and a layer of magnetic materials. According to yet another embodiment, the vibration plate is composed of an elastic resin.

With respect to still another embodiment of the present invention, the face of the vibration plate which retains the biological substances or biologically active substances is subjected to a honing process or ion-spattering process.

Preferably, the hammer bullet consists of a material having a large specific gravity, such as lead, iron or depleted uranium.

Additionally, it may be advisable and preferred to include a noise-absorbing means in the apparatus. The invention may also include a cooling system for cooling the vibration plate. In addition, the apparatus may include a vacuum means for evacuating the inside of the case, when necessary.

Therefore, the present injection apparatus is simple in operation, is compact and durable, can easily be subjected to steam sterilization or hot-air sterilization, is applicable for low pressure compressed fluid, is free from crush of the vibration plate retaining biological substances or biologically active substances, and is able to introduce the biological substances or biologically active substances into biological materials without contaminating the substances with the compressed fluid or microorganisms therein or without blowing the biological materials off. In addition, the biological materials are not damaged, because the compressed fluid does not directly contact with the biological materials to be shot-in.

In the embodiment in which a case is included, the invention includes the additional advantage of being able to control the environment for the biological materials and biological substances or biologically active substances in an isolated atmosphere from outside.

Additionally, the compressed fluid utilized in the invention is inexpensive and easily available.

Also, the fluid can be exhausted from the cylinder toward the desired place, thereby preventing exposure of the workers or the biological materials to the fluid. Additionally, the interior of the cylinder can be evacuated, thereby accelerating the speed of the hammer bullet by lowering the air resistance and reducing the impact noise.

Further, by utilizing an impact pressure of the hammer bullet of about 1 to 30 $kg/cm^2$, the apparatus can be made compact, thereby enabling it to be handy like a gun and being applicable to the human body under operation.

The inclusion of the stopper prevents damage to the vibrating plate, since the hammer bullet does not assert an excess pressure to the plate, thereby making reproducibility of introduction and reliability of the apparatus high.

In the embodiment in which the vibration plate is a flat plate and the face of the hammer bullet opposite to the vibration plate is formed to fit with the flat face of the vibration plate, the flying direction of the biological substances or biologically active substances are focused, thereby making it possible to intensively inject drugs having side effects, like anti-cancer agents, directly into the cells in the lesion without applying intravenous injection.

In the embodiment in which the vibration plate consists of a titanium alloy, the plate is not crushed by the impact and has an appropriate vibration characteristic, thereby making reproducibility for introduction high and enabling the biological substances or biologically active substances to fly with doubled acceleration.

In the embodiment in which the vibration plate is composed of a layer of titanium alloy and a layer of magnetic material, the biological substances or biologically active substances can be retained together with carriers made of magnetic materials.

In the embodiment in which the vibration plate is composed of an elastic resin, the vibration plate can be cheaply produced.

When a honing process or an ion-spattering process is applied on the face of the vibration plate retaining biological substances or biologically active substances, the biological substances or biologically active substances can be securely retained on the vibration plate without diffusion.

In the embodiment in which the hammer bullet consists of a material having a large specific gravity such as lead, iron or depleted uranium, the impact force against the vibration plate becomes large since a large amount of kinetic energy can be obtained.

When a noise-absorbing mean is provided at the other end of the cylinder, the impact noise between the hammer bullet and vibration plate can be reduced.

In the embodiment in which a cooling system for cooling the vibration plate is provided, the adhering ability of the biological substances or biologically active substances to the vibration plate is improved and the carriers can be dispersed as ice-like fine particles, even when metallic carriers are not mixed. This prevents quite temperature sensitive materials from being denatured.

In the embodiment in which the case has a vacuum means for evacuating the inside of the case, the impact force of the hammer bullet can be increased by evacuating, thereby reducing the impact noise between the hammer bullet and the vibration plate. When the vacuum means is not operating the interior of the case is at atmospheric pressure, the fragile biological materials or DNA can be handled without fear of damage and the biological substances or biologically active substances can be introduced into living animals while they are breathing, or under a normal condition without suffocation.

Other objects, features and advantages will be apparent from the following detailed description of presently preferred embodiments of the invention, given for the purpose of disclosure, and taken in conjunction with the accompanying drawings.

DETAILED DESCRIPTION OF THE PREFERRED EMBODIMENT

Figure 1:
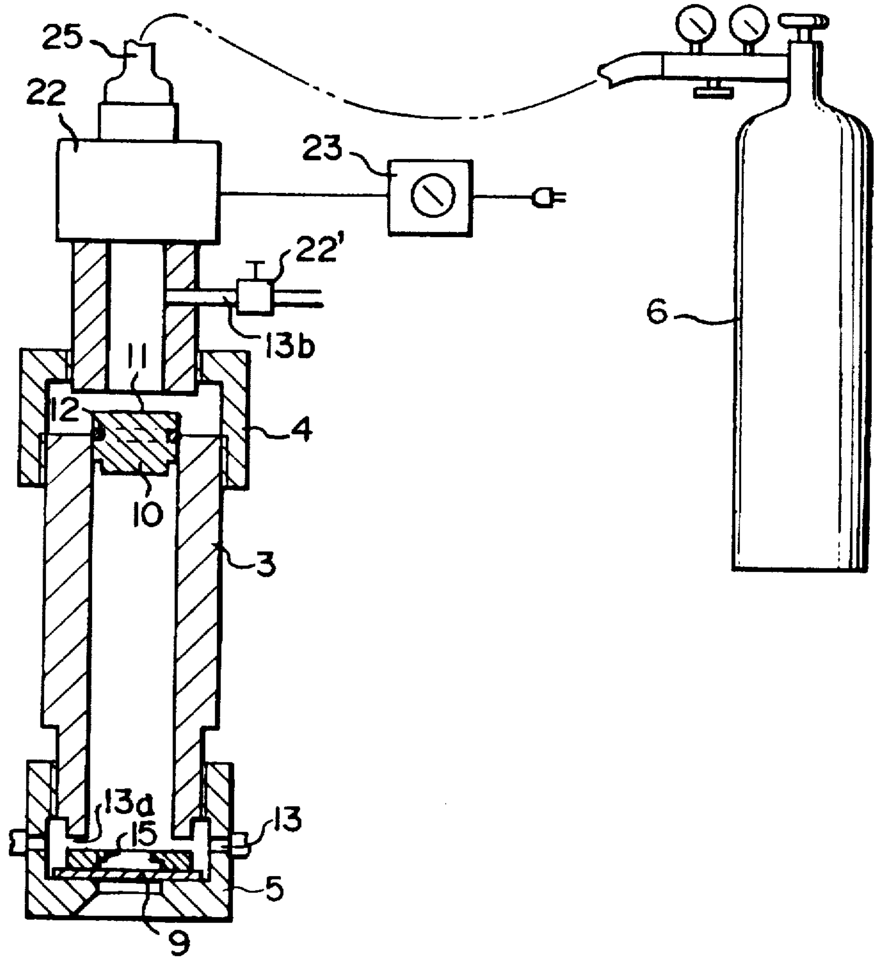
FIG. 1 is a schematic vertical section according to the first embodiment according of the present invention.

In the first embodiment according to this invention, as shown in FIGS. 1 to 4, a sealed cylinder 3 is connected to a source of compressed fluid 6. A first cap 4 is attached to one end of the cylinder 3. A flow path 25 for the compressed fluid is provided between the first cap 4 and the source of compressed fluid 6. A valve 22, along with a timer 23 for adjusting the valve's operation, is provided within the flow path. A second cap 5 is attached to the other end of the cylinder 3. A hammer bullet 10 is located within the cylinder 3 and is capable of travelling longitudinally within the cylinder between the first and second end caps. The hammer bullet 10 includes a rear face 11 facing in the direction opposite the end cap 5. A vibration plate 9 is positioned within end cap 5. The hammer bullet 10 strikes the vibration plate 9 periodically when the bullet 10 completes its longitudinal travel path from end cap 4 to end cap 5.

An exhaust port 13*b* is provided and, preferably, is situated above end cap 4 and rear face 11. Preferably, the exhaust port 13*b* is provided on the side wall of the cylinder 3. The exhaust port 13*b* includes an exhaust valve 22' for exhausting compressed fluid from the cylinder as the hammer bullet strikes the vibration plate 9. Manually operating valves are used for the exhaust valve 22', and the compressed fluid 6 filling inside of the cylinder 3 is exhausted by turning the valve open after the hammer bullet 10 contacts the vibration plate 9. The exhaust valve 22' is not limited to the manually operating parts; it also may be an electromagnetic valve which opens by detecting an output generated by a detection means that is not shown in the figure.

An aperture 13 is provided at the other end of the cylinder 3 and engages an exhaust port 13*a* for exhausting fluid in the cylinder 3 when the hammer bullet 10 contacts the vibration plate 9.

A stopper 15 is provided at the second cap 5 for receiving the hammer bullet 10 at a predetermined position so that the hammer bullet does not press the vibration plate 9 with an excess pressure.

The vibration plate 9 is a flat plate made of titanium and is formed so that the face of the hammer bullet 10 opposed to the vibration plate 9 matches the aforementioned flat face. The hammer bullet 10 is composed of materials having a high specific gravity, such as lead, iron or depleted uranium. A sealing ring 12 is fitted to the periphery of the hammer bullet 10 so that the compressed fluid does not leak beyond the hammer bullet in the direction of end cap 5. In a preferred embodiment, the cylinder 3 and the first and second caps (4 and 5, respectively) are arranged so that the free path of the hammer bullet is approximately 20 cm.

The face of the vibration plate 9 retaining biological substances 7 (DNA, for example) and biologically active substances 7' is processed into a frosted glass-like appearance by applying a honing process. An ion spattering process can also be applied.

Any of the compressed inert gases, air, water or a variety of oils may be used for the compressed fluid.

When the diameter of the hammer bullet 10 is 2 cm and the pressure of the fluid is 10 $kg/cm^2$, the impact energy impressed on the vibration plate 9 becomes about 10 kg/Fm. However, the impact pressure of the hammer bullet 10 impressed on the vibration plate 9 is adjusted in the range of 1 to 30 kg/cm$^2$ by appropriately selecting the pressure and volume of the compressed fluid 6*a*.

Alternatively, instead of using a compressed inert gas or the like as mentioned above, an appropriate amount of an explosive may be loaded on the rear face 11 of the hammer bullet 10 inside the first cap so that a desired impact force can be obtained. The hammer bullet 10 is made to collide with the vibration plate 9 by explosion of the explosive using a fire means, such as electrical ignition.

The first cap 4 and the second cap 5 are attached and hinged to the respective ends of the cylinder 3. The inner diameters of the first cap 4 and the second cap 5, and of the cylinder 3 are adjusted so as not to hinder the movement of the hammer bullet 10. The first cap 4 and the second cap 5 are removed prior to inserting the hammer bullet 10 into the predetermined position of the first cap 4. When the first cap 4 and the second cap 5 have been fitted to the cylinder 3, the hammer bullet 10 is ready for shooting. The hammer bullet 10 is retained at the predetermined position by the action of a spring on the seal ring 12 attached to the hammer bullet 10.

As for the means for supplying the compressed fluid, the valve 22, for example, an electromagnetic valve, is provided within the flow path 25 between the first cap 4 and the source of the compressed fluid 6. The compressed fluid is compressed at a prescribed pressure. The valve 22 opens for a desired time period predetermined by a timer 23 so that a desired amount of impact force is applied to the hammer bullet, thereby supplying a predetermined volume of compressed fluid.

Figure 2:
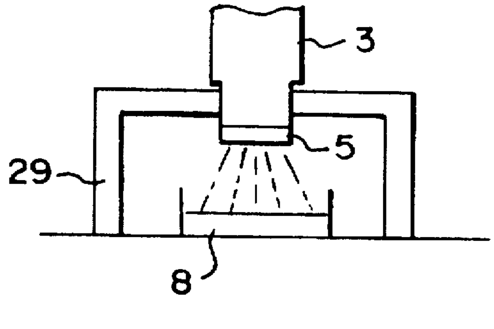
FIG. 2 shows the apparatus mounted on a fixed table according to the first embodiment of this invention.
Figure 3:
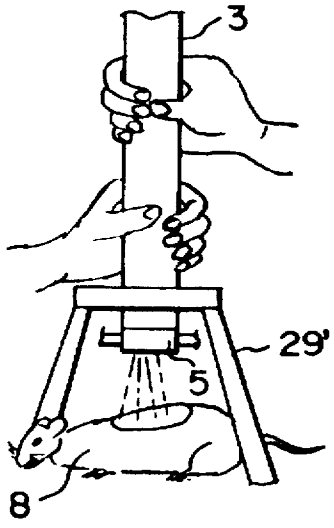
FIG. 3 shows a set state on a retaining member according to the first embodiment of this invention.

The apparatus is set on a fixing table 29 as shown in FIG. 2 and is operated by supplying the compressed fluid as described above. Depending on the biological materials 8 of concern, the cylinder 3 is held by hand after setting on a holding part 29, or simply held by hand without setting, to operate the apparatus by supplying the compressed fluid as described above.

Figure 4:
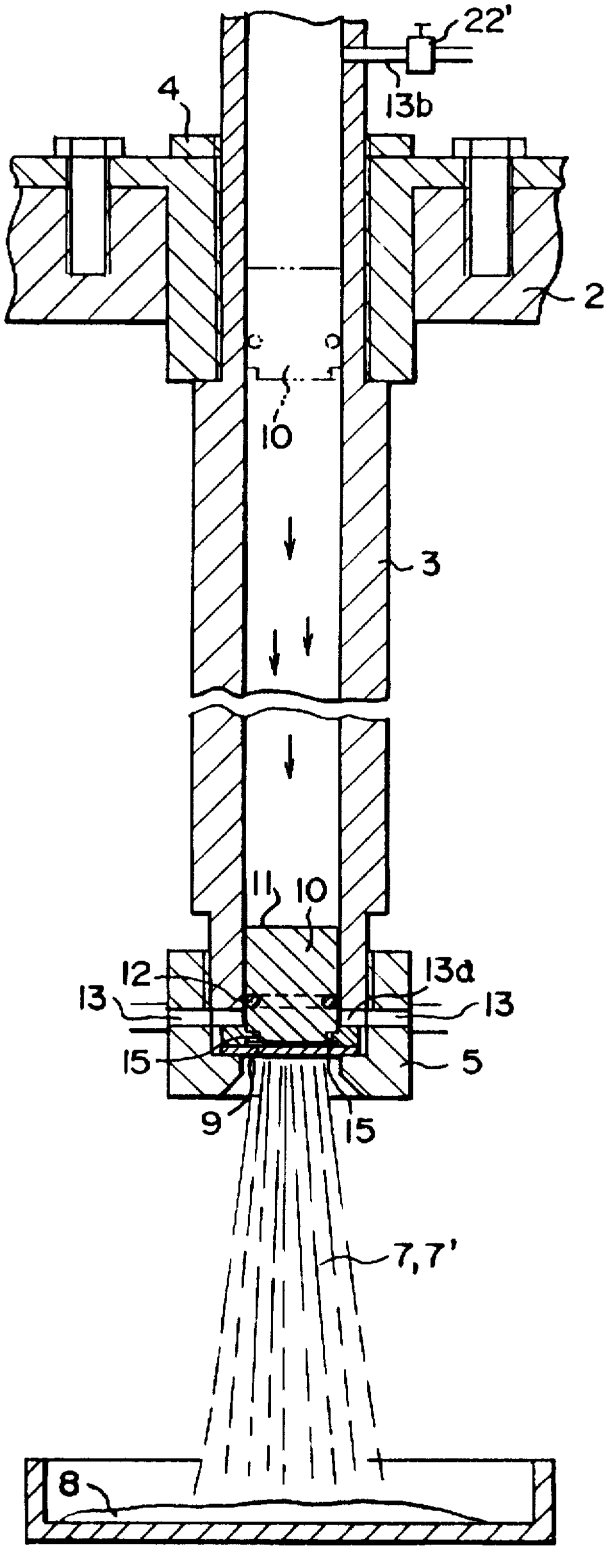
FIG. 4 illustrates the resulting spray of biological substances or biologically active substances according to the first embodiment of this invention.

The biological substances 7 or biologically active substances 7' may be mixed with fine particles (carrier) composed of gold or tungsten and having a diameter of about 1 μm together with a liquid medium like water, and the mixture is held on the face of the vibration plate 9 opposite the face which contacts the hammer bullet 10. The compressed fluid is supplied to the back face 11 of the hammer bullet 10 by operating the valve 22 for a predetermined time period, thereby moving the hammer bullet 10 to collide with the vibration plate 9. The impact between the bullet and the vibration plate 9 causes the biological substances 7 or biologically active substances 7', fine particles and liquid medium to radiate from the vibration plate 9, and introduces them into the biological material 8. Since the vibration plate 9 is a flat plate, the biological substances 7 or biologically active substances 7' move to focus on the biological material 8 as shown in FIG. 4. For the succeeding impact operation, the remaining air or the preceding liquid is exhausted from the aperture 13 via the exhaust port 13*a*, or the compressed fluid is exhausted from the exhaust port 13*b* by opening the exhaust valve 22'. The apparatus according to this invention can be used under vacuum or under atmospheric pressure.

Since the vibration plate 9 is made of a titanium alloy having very high elasticity, it is strong enough to endure the impact imparted by the collision of the face of the hammer bullet 10. The elasticity prevents loss of impact energy besides being free from contamination caused by scattering the compressed fluid toward the biological material 8. The elastic force gives the hammer bullet a complex impact pressure, which is converted into a vibration with doubled impact force and transferred to fine particles and biological substances 7 or biologically active substances 7' to accelerate them for travelling toward and colliding with the biological material 8. The accelerating force causes the biological substances 7 or biologically actives substances 7' to penetrate the cell wall membrane and to be introduced into the biological material 8. Moreover, the second cap is positioned at a predetermined location so as to contact the vibration plate 9 through a stopper 15 when the hammer bullet 10 is shot, thereby preventing the vibration plate 9 from being crushed or the biological material 8 from being contaminated or damaged. This construction makes the apparatus quite reliable.

Because a honing process may be applied to the face of the vibration plate 9 that retains the biological substances 7 or biologically active substances 7', a suspension of the biological substances or biologically active substances and fine particles of gold, platinum or tungsten with a diameter of about 1 μm in a medium like water can be retained at a predetermined position without diffusing.

Large kinetic energy of the hammer bullet 10 can be obtained since the hammer bullet 10 is made of a material having a large specific gravity like lead, iron or depleted uranium, which results in an impact force being applied when the hammer bullet 10 collides with the vibration plate 9.

According to a second embodiment of the invention, the apparatus has a similar construction to the first embodiment, except that the vibration plate 9 consists of a layer of a titanium alloy and a magnetic material. In this system, a mixture comprising the biological substances 7 or biologically active substances 7', a liquid medium and gene-retaining magnetic fine particles (carriers), as is known in the art by a disclosure in Japan Laid-Open Patent Publication HEI 6-133784, are held on the vibration plate 9 by a magnetic field. The order of lamination of the layers of the titanium alloy and magnetic material varies depending upon the operational requirements of the apparatus. For example, the titanium alloy may form the base layer and be covered by the magnetic material layer, when viewed in the direction from the top of the apparatus toward the biological material 8. In certain applications, the order may be inverted.

According to a third embodiment of the present invention, the apparatus again has a construction similar to that of the first embodiment. In this embodiment, however, the vibration plate is made from resins, such as polyimides or polyesters, having a high elasticity and having a thickness sufficient so as not to be crushed by the impact force from the hammer bullet 10. In this arrangement, a stopper 15 is provided at a predetermined position on the second cap 5 where the hammer bullet 10 contacts the vibration plate 9 to assure that the vibration plate 9 is not excessively pressed by the hammer bullet 10. Moreover, since vibration plate 9 is protected from being crushed and the compressed fluid does not leak due to the close contact between the seal ring 12 and the cylinder 3, the biological material is free from contamination.

Figure 5:
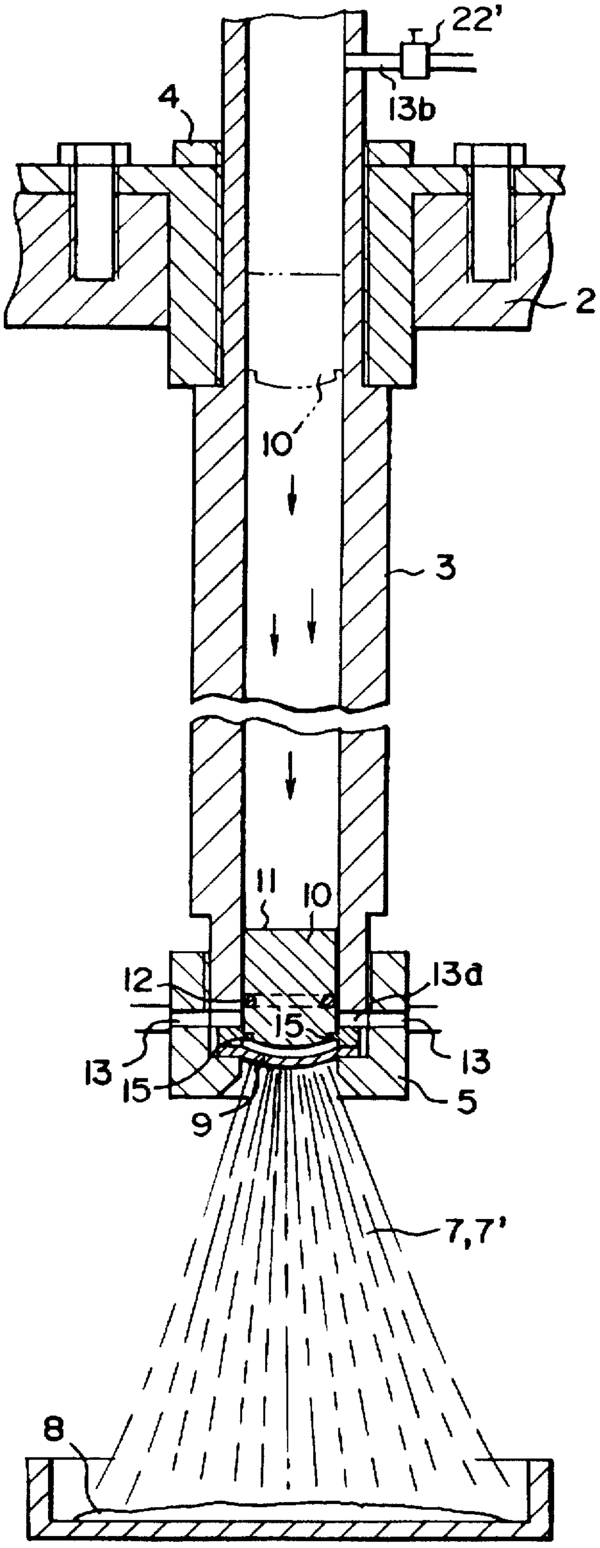
FIG. 5 is a schematic vertical cross section of the present apparatus according to the fourth embodiment of this invention.

In a fourth embodiment of the present invention, the apparatus has a similar construction to that of the first embodiment, except that the vibration plate 9 instead of having a flat plate profile is formed into a convex plate along the direction of radiation of the biological substances 7 or biologically active substances 7', as shown in FIG. 5. The face of the hammer bullet 10 which engages the vibration plate 9 is also formed so as to fit with the convex face of the vibration plate 9. In this construction, the biological substances 7 or biologically active substances 7' are radiated with a little wider radiation angle than that in the first embodiment when the hammer bullet 10 is made to collide with the vibration plate 9. This enables the substances to be introduced into the biological material 8 with a wider distribution. Therefore, the method is effective when one desires to introduce the biological substances or biologically active substances into the biological material in a wide range.

Figure 6:
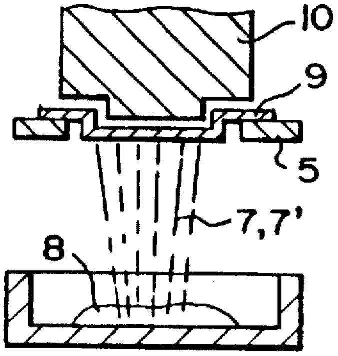
FIG. 6 is a schematic vertical cross section of the present invention according to the fifth embodiment of this invention.

In the fifth embodiment according to this invention having a similar construction with that in the first embodiment, the vibration plate 9 is formed into a stepped convex plate along the direction of radiation of the biological substances 7 or biologically active substances 7', as shown in FIG. 6. The face of the hammer bullet 10 opposite to the vibration plate 9 is also formed so as to fit with the convex face of the vibration plate 9. In this construction, the biological substances 7 or biologically active substances 7' are radiated with a more concentrated radiation angle to the center than that in the first embodiment when the hammer bullet 10 is made to collide with the vibration plate 9. This construction enables the apparatus to introduce the substances deep into the center of the biological material 8. Therefore, the method is effective when one desires to introduce the biological substances 7 or biologically active substances 7' deep into the center of the biological material 8.

Figure 7:
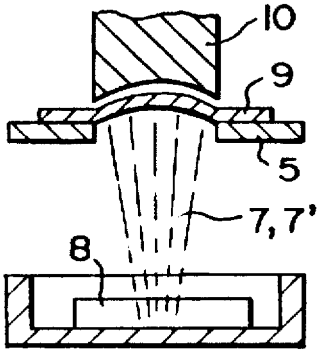
FIG. 7 is a schematic vertical cross section of the present invention according to the sixth embodiment of this invention.

In the sixth embodiment according to this invention having a similar construction with that in the first embodiment, the vibration plate 9 is formed into a concave plate along to the direction of radiation of the biological substances 7 or biologically active substances 7', as shown in FIG. 7. The face of the hammer bullet 10 which engages the vibration plate 9 is also formed so as to fit with the concave face of the vibration plate 9. In this construction, when the hammer bullet 10 collides with the vibration plate 9, the biological substances 7 or biologically active substances 7' are radiated in a more concentrated radiation angle to the center than the first embodiment. This more concentrated spray pattern enables the substances to be introduced deep into the center of the biological material 8. Therefore, the method is effective when one desires to introduce the biological substances 7 or biologically active substances 7' deep into the center of the biological material 8.

Figure 8:
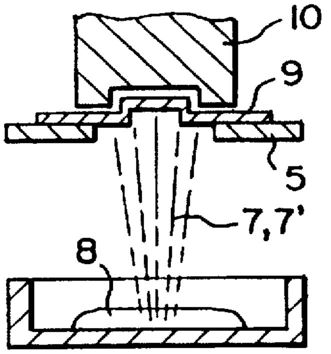
FIG. 8 is a schematic vertical cross section of the present invention according to the seventh embodiment of this invention.

In a seventh embodiment according to this invention having a similar construction with that in the first embodiment, the vibration plate 9 is formed into a stepped concave plate along to the direction of radiation of the biological substances 7 or biologically active substances 7', as shown in FIG. 8. The face of the hammer bullet 10 that contacts the vibration plate 9 is also formed so as to fit with the concave face of the vibration plate 9. In this construction, when the hammer bullet 10 collides with the vibration plate 9, the biological substances 7 or biologically active substances 7' are radiated in more concentrated radiation angle to the center than that in the first embodiment, enabling introduction of the substances deep into the center of the biological material 8. Therefore, the method is effective when one desires to introduce the biological substances 7 or biologically active substances 7' deep into the center of the biological material 8.

Figure 9:
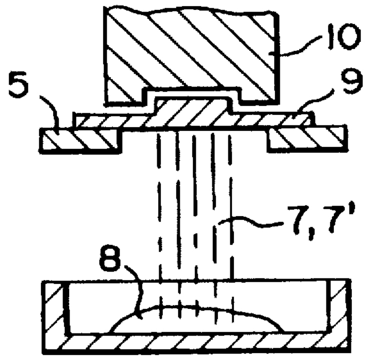
FIG. 9 is a schematic vertical cross section of the cylinder according to the eighth embodiment of this invention.

In an eighth embodiment according to this invention having a similar construction with that in the first embodiment, a protrusion is formed on the vibration plate 9 along the direction of the hammer plate 10, as shown in FIG. 9. The face of the hammer bullet 10 that contacts to the vibration plate 9 is also formed so as to fit with the protrusion of the vibration plate 9. In this construction, when the hammer bullet 10 collides with the vibration plate 9, the biological substances 7 or biologically active substances 7' are radiated in a smaller radiation angle than that in the first embodiment, enabling the introduction of the substances deep into the center and shallow along the periphery of the biological material 8. Therefore, the method is effective when one desires to introduce the biological substances 7 or biologically active substances 7' deep into the center and shallow along the periphery of the biological material 8.

Figure 10:
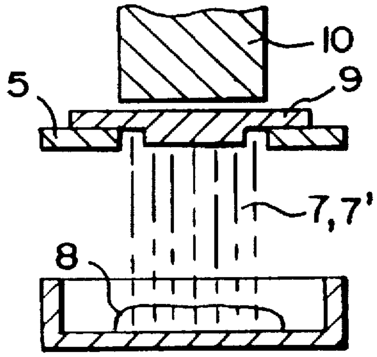
FIG. 10 is a schematic vertical cross section of the cylinder according to the ninth embodiment of this invention.

In a ninth embodiment according to this invention having a similar construction with that in the first embodiment, a protrusion is formed on the vibration plate 9 along the direction of the hammer plate 10, as shown in FIG. 10. The face of the hammer bullet 10 that contacts the vibration plate 9 is formed into a flat plate. In this construction, when the hammer bullet 10 collides with the vibration plate 9, the biological substances 7 or biologically active substances 7' are radiated in a smaller radiation angle than that in the first embodiment, enabling the introduction of the substances deep into the center and shallow along the periphery of the biological material 8. Therefore, the method is effective when one desires to introduce the biological substances 7 or biologically active substances 7' deep into the center and shallow along the periphery of the biological material 8.

Figure 11:
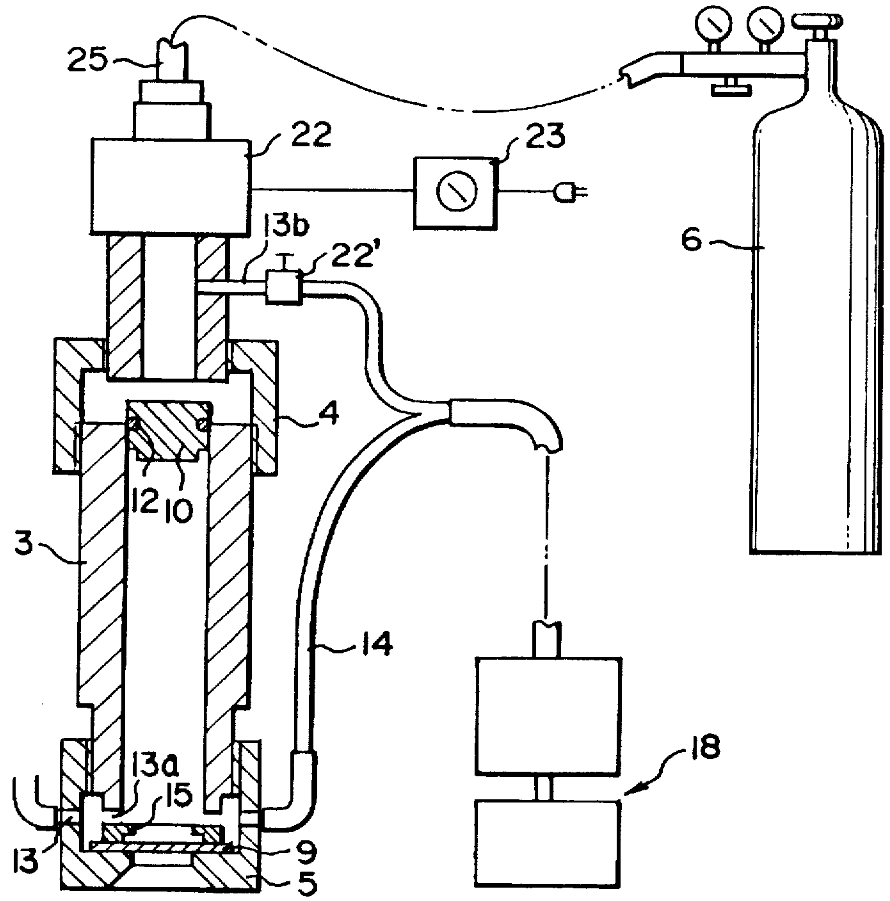
FIG. 11 is a schematic vertical cross section of the cylinder according to the tenth embodiment of this invention.

In a tenth embodiment according to this invention, the aperture 13 and the exhaust port 13*b* are connected by providing a duct 14 as shown in FIG. 11. In this construction, the remaining air to be exhausted from the cylinder 3 and the supplied compressed fluid can be exhausted to a desired location, making it possible to protect the biological material and workers from the aforementioned exhausted fluid. A vacuum means 18 for evacuating the inside of the cylinder 3 may be conveniently provided at the duct 14. The hammer bullet 10 is made to move smoothly toward the vibration plate 9 when the inside of the cylinder 3 is evacuated, thereby reducing the impact noise accompanying the collision of the hammer bullet and the vibration plate 9.

Figure 12:
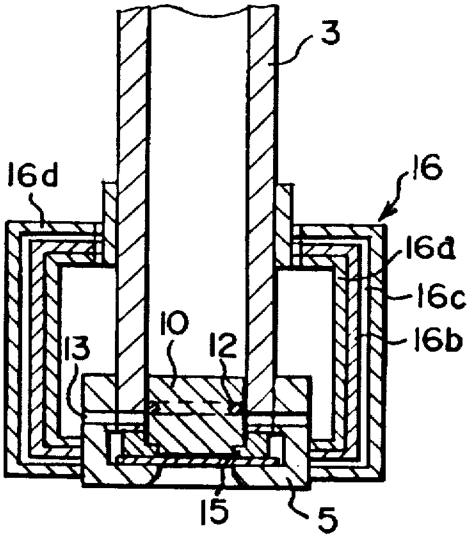
FIG. 12 is a schematic vertical cross section of the cylinder according to the eleventh embodiment of this invention.

In an eleventh embodiment according to this invention, the bottom portion of the cylinder 3 and the second cap 5 are covered by a noise-absorbing means 16 as shown in FIG. 12. The noise absorbing means 16 is composed of a noise proof layer of wool 16*a*, a gypsum board layer 16*b*, a lead layer 16*c* and an iron layer 16*d* as seen from the side wall of the cylinder 3. This noise-absorbing means 16 reduces the impact noise generated from collision of the hammer bullet 10 with the vibration plate 9. The duct 14, vacuum means 18, and noise-absorbing means 16 are appropriately attached depending on the operating conditions and work environment.

Figure 13:
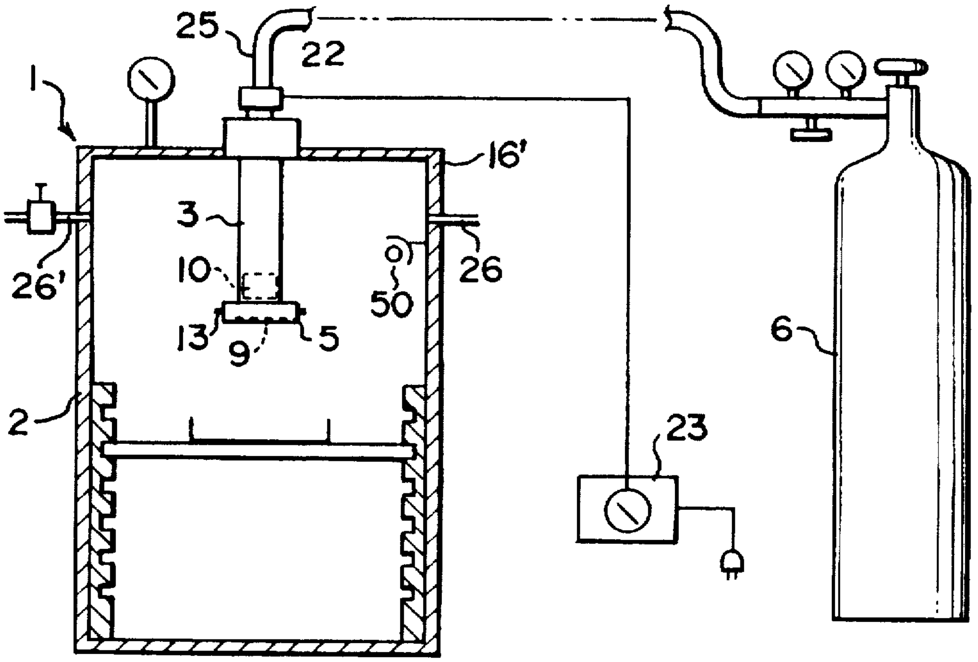
FIG. 13 is a schematic vertical cross section of the cylinder according to the twelfth embodiment of this invention.
Figure 14:
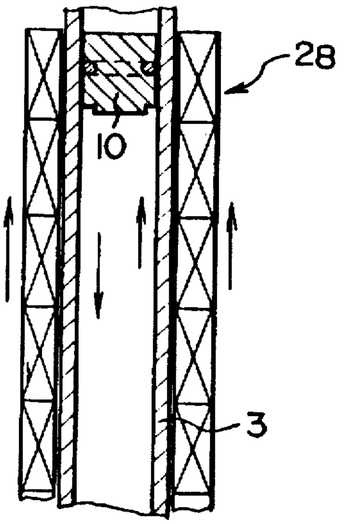
FIG. 14 is a schematic vertical cross section in which a linear motor is provided in the cylinder portion according to the twelfth embodiment of this invention.

According to a twelfth embodiment of this invention, a case 2 for mounting a cylinder 3 is provided. This embodiment is depicted in FIG. 13. The case 2 includes an exhaust port 26 having a valve (not shown) and a ventilation port 26' also having a valve. A manual valve or an electromagnetic valve that is operated by instruction signals is used for the valve attached to the ventilation port 26'. A noise-absorbing material 16' around the periphery or inner wall of the case 2, and a light source 50, as necessary for keeping alive the biological material 8 in the case 2, may also be provided. A linear motor driven moving device using electromagnetic power as shown in FIG. 14, or an elevator mechanism driven by electromagnetic power (not shown), instead of manual means, may be mounted on the cylinder 3 for moving the hammer bullet 10 to a predetermined position in the first cap 4. For example, in the case of a linear motor driven moving device, electromagnetic power is generated in coil 28 (see FIG. 14) and the resulting power source moves gradually upwardly, thus raising the hammer bullet to a predetermined position.

In this arrangement, the remaining fluid in the cylinder 3 is exhausted from the aperture 13 and the exhaust port **13*b*, and the compressed fluid is exhausted toward the direction of the case 2, and finally exhausted from the exhaust port 26 to outside of the case 2. Since the fluid is not exhausted toward the direction of the biological material 8, there are no problems with contaminating or damaging the biological material 8. During the preparation step for operating the apparatus, a required volume of gas ($CO_2$, $O_2$, NO, $NO_2$, $SO_2$ or steam) necessary for the biological material 8 is supplied by turning the valve of the ventilation port 26' open. After shutting the valve, the environmental condition is controlled by illuminating a light beam from the light source 50 so that the biological material 8 and the biological substances 7 or biologically active substances 7' are not dried or do not die out. In this case, the valve of the exhaust port 26 is initially closed, but then opens to exhaust the compressed fluid after the fluid has been supplied and the hammer bullet 10 has collided with the vibration plate 9. The compressed fluid exhausted does not damage the biological material 8 since the interior of the case 2 is filled with gas like $CO_2$. The provision of a noise-absorbing material to the case prevents noise from being generated when the remaining fluid in the cylinder 3** is exhausted.

Figure 15:
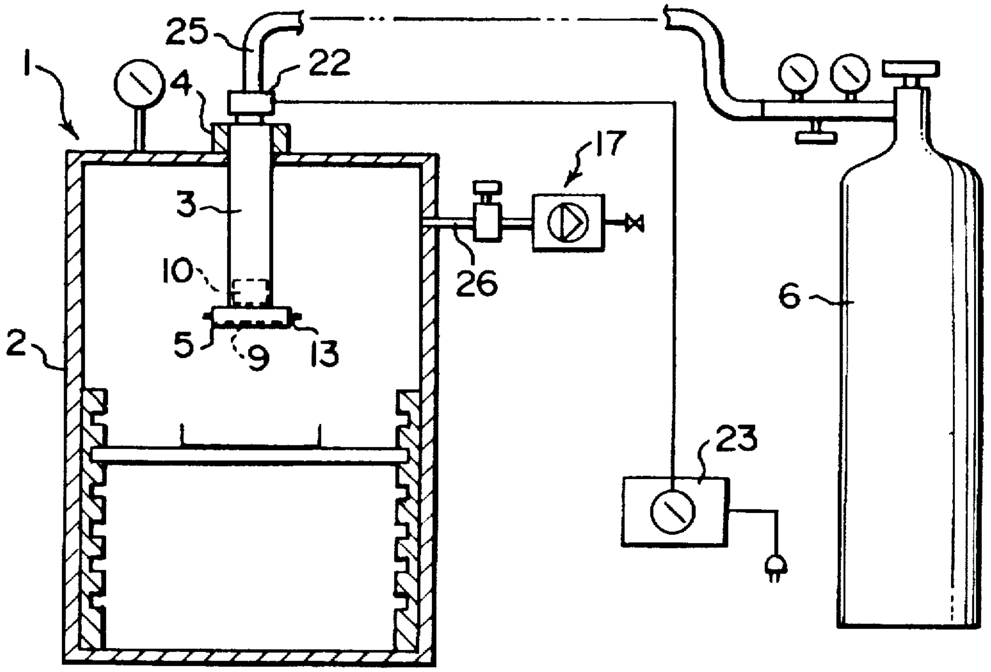
FIG. 15 is a schematic vertical cross section according to the thirteenth embodiment of this invention.

In a thirteenth embodiment according to this invention, a vacuum means 17 is provided at the exhaust port 26 of the case 2, as shown in FIG. 15. When the interior of the case 2 is evacuated, the impact force can be increased by improving the suction efficiency of the hammer bullet 10, as well as reducing the noise of collision between the hammer bullet 10 and the vibration plate 9 and the exhaust noise of a compressed fluid, thereby preventing noise pollution.

Figure 16:
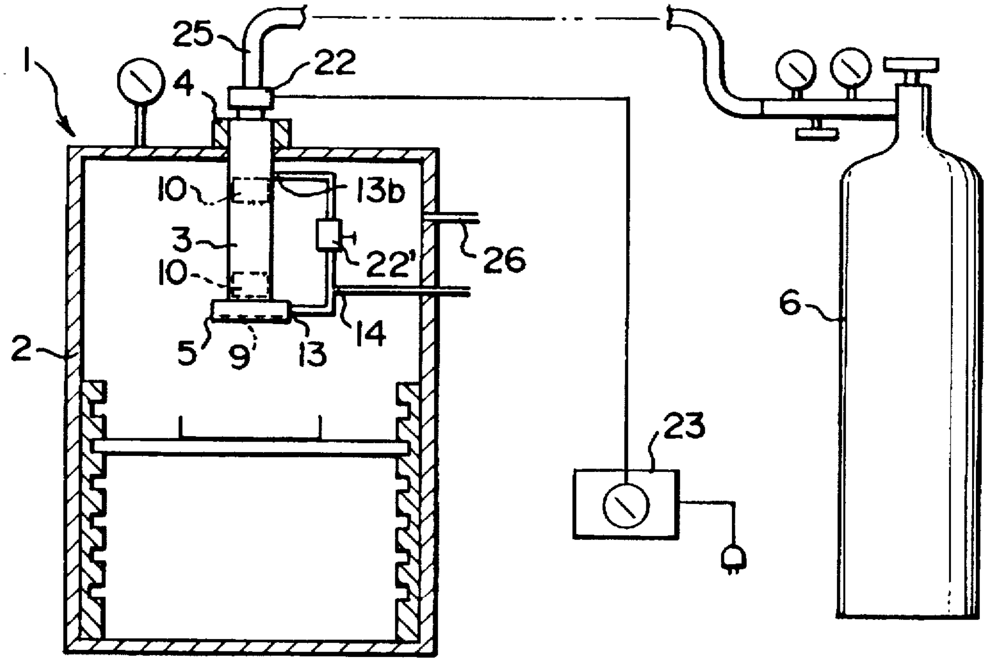
FIG. 16 is a schematic vertical cross section according to the fourteenth embodiment of this invention.

A fourteenth embodiment according to this invention is shown in FIG. 16. A duct 14 is provided for exhausting to the outside of the case the air in the cylinder 3 and any remaining compressed fluid. In this system, the air in the cylinder 3, the remaining fluid exhausted from the aperture 13 and exhaust port **13*b* and any compressed fluid can be directly exhausted outside of the case 2 without having to evacuate the inside of the case, thereby preventing contamination inside the case 2. When the interior of the cylinder 3 is evacuated without evacuating the inside of the case 2, impact force can be increased by improving the suction efficiency of the hammer bullet 10, in addition to preventing DNA or biological material from being denatured by evaporation of moisture. Especially advantageous according to this embodiment is the fact that the biological substances 7 or biologically active substances 7' can be introduced into living animals while they are breathing, or otherwise under normal conditions without suffocation. A filter for cleaning the exhausted fluid may be provided at the exhaust port of the duct 14**.

Figure 17:
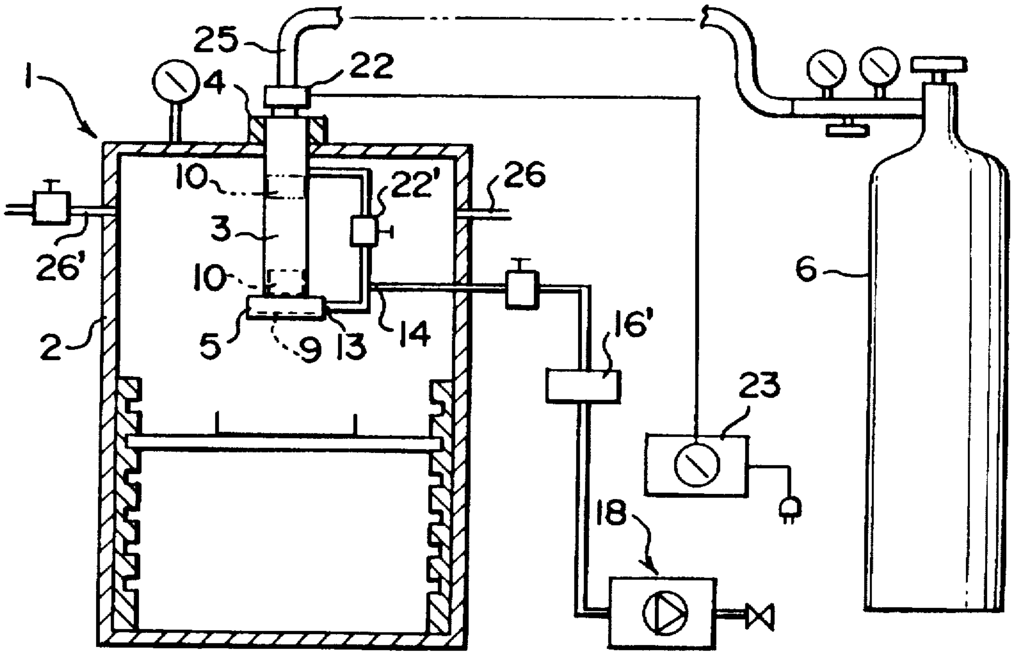
FIG. 17 is a schematic vertical cross section according to the fifteenth embodiment of this invention.

A fifteenth embodiment according to this invention is shown in FIG. 17. A vacuum means 18 is provided outside of the case 2 and in the middle of the duct 14. This vacuum means 18 increases the impact force between the hammer bullet 10 and vibration plate 9, as well as reducing the noise, such as exhaust noise, of the compressed fluid or impact noise between the hammer bullet 10 and vibration plate 9. A noise-absorbing means 16' may be provided at outside of the case 2, at the middle of the duct 14 and between the case 2 and vacuum means 18. This noise-absorbing means 16' is a noise-absorbing muffler, which is more effective in reducing the noise, such as the exhaust noise of the compressed fluid or impact noise between the hammer bullet 10 and vibration plate 9.

Figure 18:
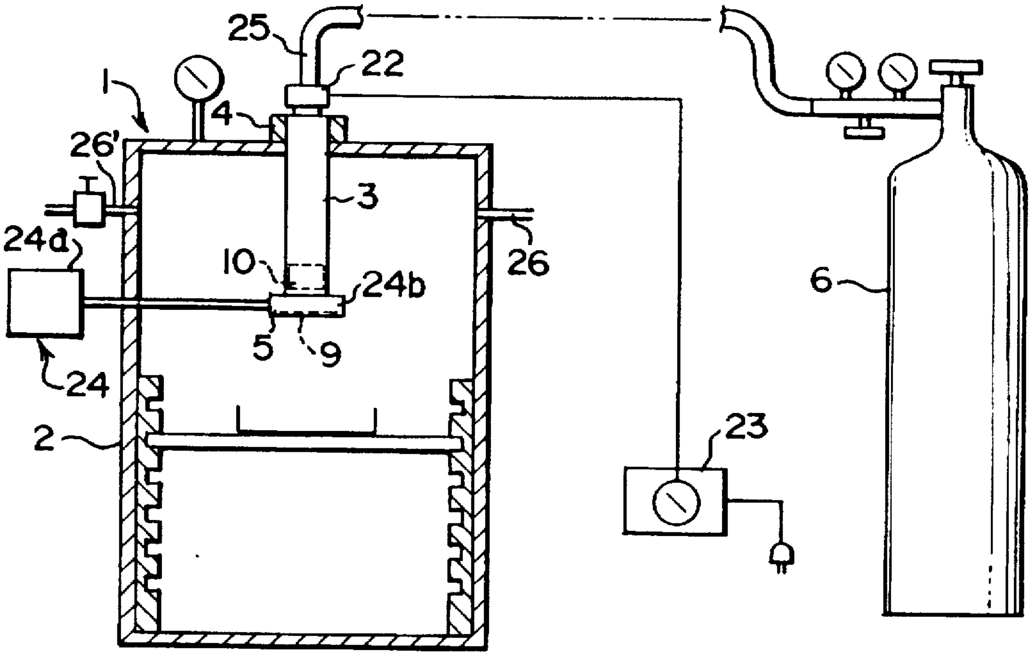
FIG. 18 is a schematic vertical cross section according to the sixteenth embodiment of this invention.

In a sixteenth embodiment according to this invention as shown in FIG. 18, a cooling system 24, composed of a cooler **24*a* and heat exchanger 24*b*, is provided around the periphery of the second cap 5. This heat exchanger 24*b* is connected to the cooler 24*a* placed outside of the case 2. In this system, the second cap 5 is cooled below the freezing point by operating the cooler 24*a* while keeping the temperature of the vibration plate 9 below the freezing point. The biological substances 7 or biologically active substances 7' are mixed with the liquid medium and the mixture is frozen. When the vibration plate is impacted, the frozen mixture is broken into frozen fine particles and sprayed toward the biological material 8 to introduce the biological substances 7 or biologically active substances 7'. Fine metallic particles (carriers) are not necessary because the biological substances 7 or biologically active substances 7' are frozen together with the liquid medium to form fine ice particles. Either a cooling method of circulating the cooling medium or an electronic cooling method using Peltier effect may be applied for the cooling system 24. The system using the electronic cooling method may be applied to the cylinder 3**.

The thirteenth, fifteenth and sixteenth embodiments may be used in combination with each other.

Figure 19:
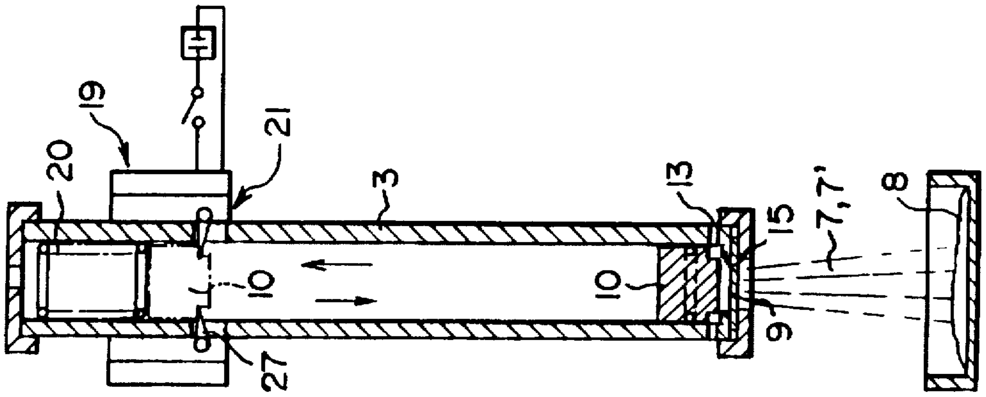
FIG. 19 is a schematic vertical cross section according to the seventeenth embodiment of this invention.

In a seventeenth embodiment according to this invention as illustrated in FIG. 19, the source of the compressed fluid 6, the flow path 25, the first cap 4 and the second cap 5 are eliminated from the apparatus. Instead, driving means 19 is provided at one end of the cylinder 3 for moving the hammer bullet 10. As is the case in the first embodiment, a vibration plate 9 is attached at the other end of the cylinder 3. A stopper 15 for receiving the hammer bullet 10 is provided at a predetermined position so that the bullet does not collide so strongly with the vibration plate 9 and does not apply too large of an impact pressure to the vibration plate 9. The driving means 19 includes a compressed spring 20 and a trigger mechanism 21 for holding the compressed spring 20 in a compressed state and for releasing the hammer bullet 10 once a triggering signal is received. The trigger mechanism 21 includes a backstop 27 for holding the hammer bullet in a ready position and for releasing the tension on the compressed spring 20 and the bullet upon receipt of an electromagnetic signal. A noise-absorbing means may be provided at the other end of the cylinder 3.

In this mechanism, the cylinder 3 may be held by a fixing table 29 and a holding part 29' or manually as shown in the first embodiment. When the compressed spring is released from the compressed waiting state by the action of the trigger mechanism, the hammer bullet 10 moves along the guide on the holding part 29' to impact the vibration plate 9. This collision gives the vibration plate 9 an impact and the biological substances 7 or biologically active substances 7' are made to radiate from the vibration plate 9 for introducing them into the biological material 8.

Figure 20:
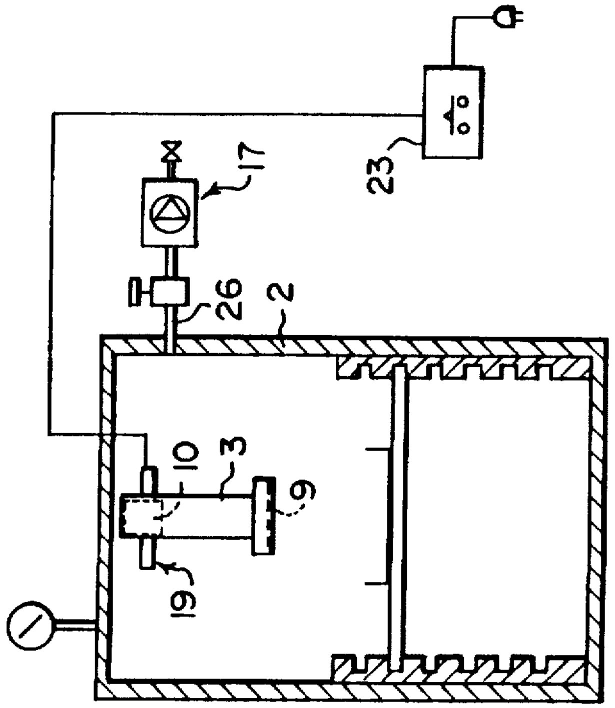
FIG. 20 is a schematic vertical cross section according to the eighteenth embodiment of this invention.

In the eighteenth embodiment according to this invention as shown in FIG. 20, a case 2 for mounting the cylinder 3 is provided. A vacuum means and a light source may be provided in the case 2, or a noise-absorbing means may be provided in the cylinder 3. In addition, a linear motor drive mechanism as shown in FIG. 14 or an elevator mechanism (not shown) also may be provided for settling the hammer bulletin 10 at a predetermined position. The hammer bullet can be moved by the mechanical means, like a compressed spring or by the linear motor drive to collide with the vibration plate 9. By this mechanism, the biological substances or the biologically active substances can be radiated after controlling the isolated environment for the biological material 8 or for the biological substances 7 or biologically active substances 7' in the case 2. When a vacuum means 17 is provided in the case 2, moisture in the biological material or in the biological substances 7 or biologically active substances 7' can be evaporated when necessary. The impact noise between the hammer bullet and the vibration plate also can be reduced by applying the vacuum means.

Figure 21:
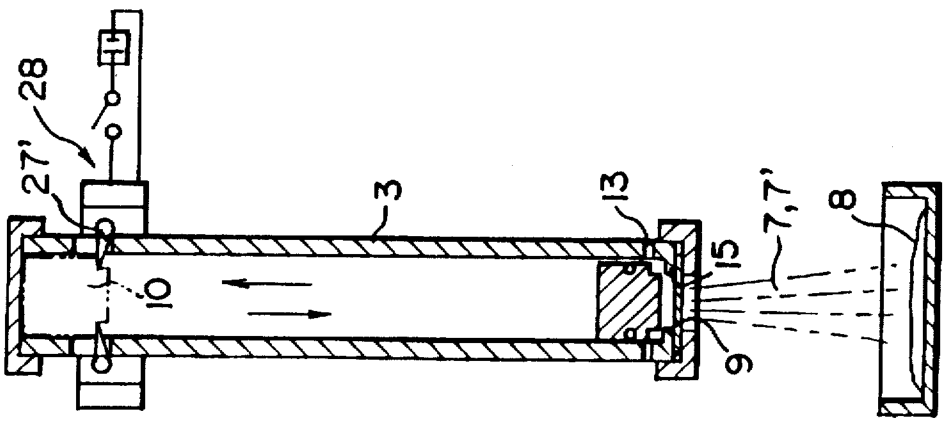
FIG. 21 is a schematic vertical cross section according to the ninth embodiment of this invention.
Figure 23:
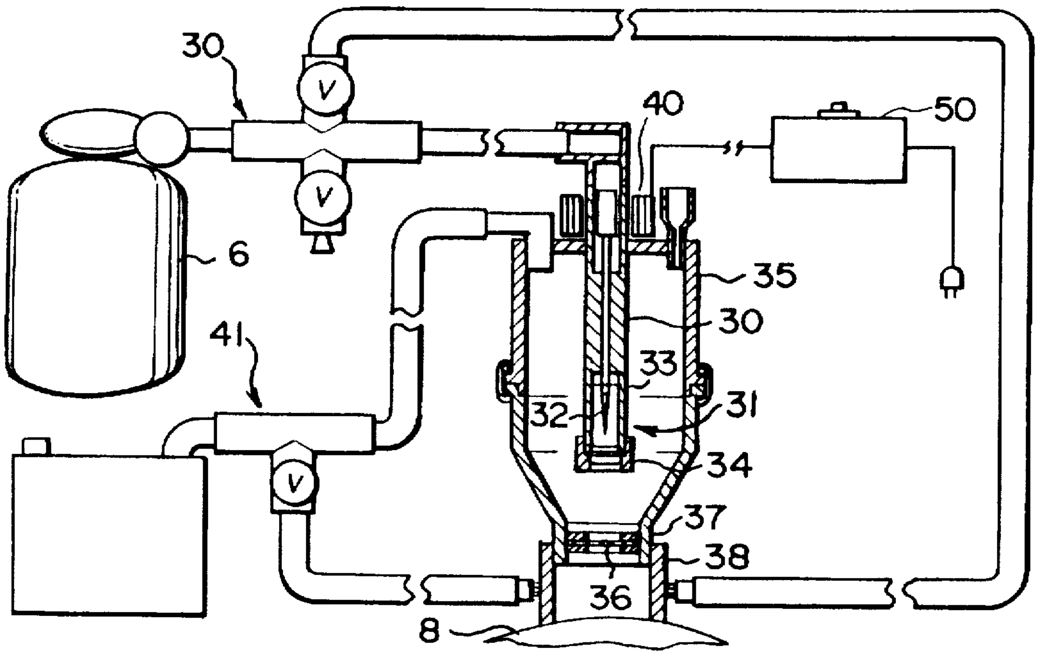
FIG. 23 is a schematic cross section of the conventional injection apparatus.
Figure 24:
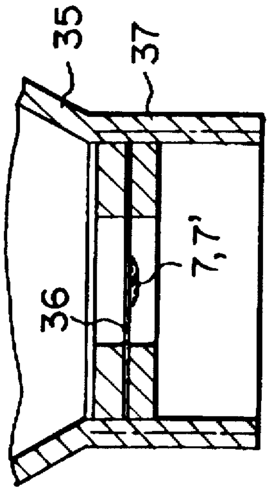
FIG. 24 is a schematic cross section of this invention indicating a state in which the membrane retains biological substances or biologically active substances.
Figure 25:
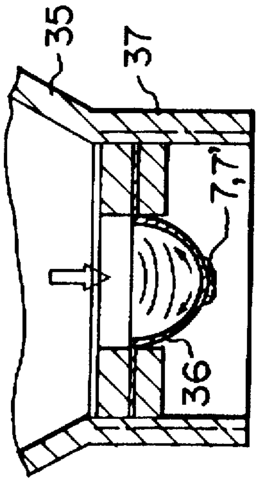
FIG. 25 is a schematic cross section of this invention indicating a state in which the membrane is extruded toward the biological material by the pressure of the fluid.
Figure 26:
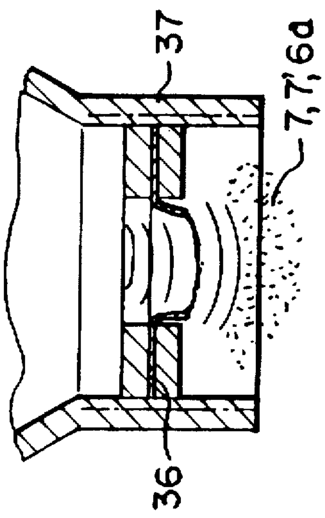
FIG. 26 is a schematic cross section of this invention indicating a state in which biological substances or biologically active substances are travelling with acceleration toward the biological material.
Figure 27:
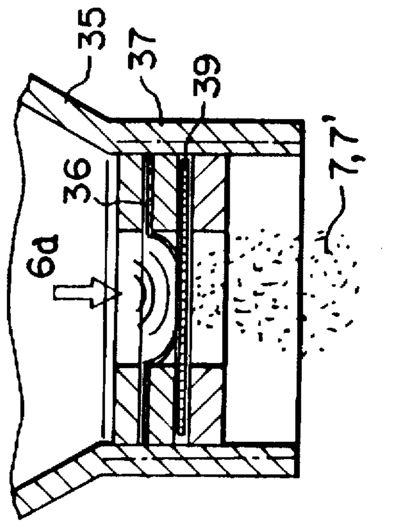
FIG. 27 is a schematic vertical cross section indicating a state in which the screen prevents the membrane from being blasted.

In the nineteenth embodiment according to this invention as shown in FIG. 21, the compressed fluid source 6, flow path 25, the first cap attached at one end of the cylinder 3 and the second cap 5 are eliminated. A holding part 28 is provided with backstop 27' for stopping or releasing the hammer bullet 10. As in the first embodiment, the cylinder 3 is provided with a hammer bullet 10 and a vibration plate 9 situated at the bottom of one end of the cylinder 3. A stopper 15 that receives the hammer bullet 10 at a predetermined position so that the bullet does not give an excess pressure to the vibration plate 9 when the hammer bullet 10 collides with the vibration plate. A noise absorbing means may be provided at the other end of the cylinder 3.

In this system, the hammer bullet 10 freely falls down in the cylinder 3 at a desired time to collide with the vibration plate 9 by opening the backstop 27' for releasing the hammer bullet 10 after the hammer bullet 10 has been set at a predetermined position. An impact is given to the vibration plate 9 by this collision, thereby radiating the biological substances 7 or biologically active substances 7' from the vibration plate 9 to introduce them into the biological material 8.

Figure 22:
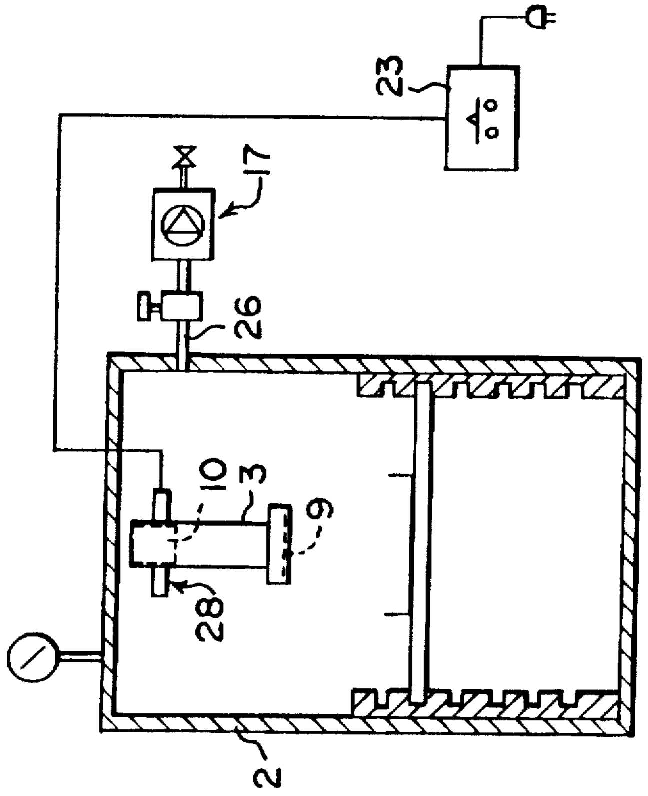
FIG. 22 is a schematic vertical cross section according to the twentieth embodiment of this invention.

In the twentieth embodiment according to this invention as shown in FIG. 22, a case 2 is provided for mounting the cylinder 3. A vacuum means 17 and a light source for breeding the biological materials in the case 2 and a noise-absorbing means in the cylinder 3 may be provided. In addition, a linear motor drive mechanism as shown in FIG. 14 or an elevator mechanism (not shown) may also be provided for setting the hammer bullet 10 at a predetermined position. By this mechanism, the biological substances 7 or the biologically active substances 7' can be radiated from the vibration plate 9 and introduced into the biological material 8 by an impact force generated by a collision between the freely falling hammer bullet 10 and the vibration plate 9 after controlling the isolated environment for the biological material 8 or for the biological substances or biologically active substances in the case 2. When a vacuum means 17 is provided in the case 2, moisture in the biological material or in the biological substances or biologically active substances can be evaporated when necessary. The impact noise between the hammer bullet and the vibration plate can also be reduced by applying the vacuum mean.

Therefore, the present injection apparatus is simple in operation, is compact and durable, can easily be subjected to steam sterilization or hot-air sterilization, is applicable for low pressure compressed fluid, is free from crush of the vibration plate retaining biological substances or biologically active substances, and is able to introduce the biological substances or biologically active substances into biological materials without contaminating the substances with the compressed fluid or microorganisms therein or without blowing the biological materials off. In addition, the biological materials are not damaged because the compressed fluid does not directly contact the biological materials.

In the embodiment in which a case is included, the invention includes the additional advantage of being able to control the environment for the biological materials and biological substances or biologically active substances in an isolated atmosphere from outside.

Additionally, the compressed fluid utilized in the invention is inexpensive and easily available.

Also, the fluid can be exhausted from the cylinder 3 toward a desired place, thereby preventing the biological materials or workers from being exposed to the fluid. Additionally, the interior of the cylinder can be evacuated, thereby accelerating the speed of the hammer bullet by lowering the air resistance, in addition to reducing the impact noise.

Further, by utilizing an impact pressure of the hammer bullet of about 1 to 30 $kg/cm^2$, the apparatus can be made compact, thereby enabling it to be handy like a gun and being applicable to the human body under operation.

The inclusion of the stopper prevents damage to the vibrating plate since the hammer bullet does not exert an excessive pressure to the plate, thereby making reproducibility of injection and reliability of the apparatus high.

In the embodiment in which the vibration plate is a flat plate and the face of the hammer bullet opposite to the vibration plate is formed to fit with the flat face of the vibration plate, the spraying direction of the biological substances or biologically active substances are focused, thereby making it possible to intensively inject drugs having side effects, like anti-cancer agents, directly into the cells in the lesion without applying intravenous injection.

In the embodiment in which the vibration plate consists of a titanium alloy, the plate is not crushed by the impact and has an appropriate vibration characteristic, thereby making reproducibility for injection high and enabling the biological substances or biologically active substances to spray with doubled acceleration.

In the embodiment in which the vibration plate is composed of a layer of titanium alloy and a layer of magnetic material, the biological substances or biologically active substances can be retained together with carriers made of magnetic materials.

In the embodiment in which the vibration plate is composed of an elastic resin, the vibration plate can be cheaply produced.

When a honing process or an ion-spattering process is applied on the face of the vibration plate retaining biological substances or biologically active substances, the biological substances or biologically active substances can be securely retained on the vibration plate without diffusion.

In the embodiment in which the hammer bullet consists of a material having a large specific gravity such as lead, iron or depleted uranium, the impact force against the vibration plate becomes large since a large amount of kinetic energy can be obtained.

When a noise-absorbing mean is provided at the other end of the cylinder, the impact noise between the hammer bullet and vibration plate can be reduced.

In the embodiment in which a cooling system for cooling the vibration plate is provided, the adhering ability of the biological substances or biologically active substances to the vibration plate is improved. Additionally, the carriers can spray in the form of ice-like fine particles even when any metallic carriers are not mixed, thereby preventing quite temperature sensitive materials from being denatured.

In the embodiment in which the case has a vacuum means for evacuating the inside of the case, the impact force of the hammer bullet can be increased by evacuating the cylinder, thereby reducing the impact noise between the hammer bullet and the vibration plate. When the vacuum means is not operating and the interior of the case is at atmospheric pressure, the fragile biological materials or DNA can be handled without fear of damage and the biological substances or biologically active substances can be introduced into living animals while they are breathing, or otherwise under a normal condition without suffocation.

The present invention, therefore, is well adapted to carry out the objects and attain the ends and advantages mentioned, as well as others inherent therein. While presently preferred embodiments of the invention have been given for the purpose of disclosure, numerous changes in the details of construction, arrangement of parts, and steps of the process, which will readily suggest themselves to those skilled in the art and which are encompassed within the spirit of the invention and the scope of the appended claims, may be made.

What is claimed is:

1. An apparatus for injecting biological substances or biologically active substances into a biological material, comprising:

a single sealed cylinder;

a compressed fluid source connected to one end of said cylinder;

a vibration plate attached to the other end of said cylinder;

a hammer bullet provided in said cylinder;

a flow path provided between said compressed fluid source and said cylinder; and a valve provided within said flow path, wherein compressed fluid from said compressed fluid source moves said hammer bullet into contact with said vibration plate and causes biological substances or biologically active substances retained on the face of said vibration plate opposite the face contacted by said hammer bullet to radiate from said vibration plate.

2. An apparatus as claimed in claim 1, further comprising a case for mounting said cylinder.

3. An apparatus as claimed in claim 1, wherein said compressed fluid is an inert gas, air, water, or a variety of oils.

4. An apparatus as claimed in claim 1, further comprising at least one duct at each end of said cylinder for discharging from the cylinder any excess fluid remaining after said hammer bullet strikes said vibration plate.

5. An apparatus as claimed in claim 4, further comprising vacuum means connecting to said ducts for evacuating said cylinder.

6. An apparatus as claimed in claim 1, wherein said compressed fluid source provides an impact pressure to said hammer bullet of about 1 to 30 $kg/cm^2$.

7. An apparatus as claimed in claim 1, further comprising a stopper positioned at the same end of said cylinder as said vibration plate for stopping said hammer bullet at a predetermined position.

8. An apparatus as claimed in claim 1, wherein said vibration plate is substantially flat and the face of said hammer bullet opposite to said vibration plate is formed to fit with the flat face of said vibration plate.

9. As apparatus as claimed in claim 1, wherein said vibration plate comprises a titanium alloy.

10. An apparatus as claimed in claim 1, wherein said vibration plate is comprises a layer of titanium alloy and a layer of magnetic material.

11. An apparatus as claimed in claim 1, wherein said vibrating material comprises an elastic resin.

12. An apparatus as claimed in claim 1, wherein the face of said vibration plate that retains the biological substances or biologically active substances is honed.

13. An apparatus as claimed in claim 1, wherein the face of said vibration plate that retains the biological substances or biologically active substances is ion spattered.

14. An apparatus as claimed in claim 1, wherein said hammer bullet comprises a material having a large specific gravity.

15. An apparatus as claimed in claim 14, wherein said hammer bullet comprises a material selected from lead, iron or depleted uranium.

16. An apparatus as claimed in claim 1, further comprising a noise-absorbing means at the same end of said cylinder as said vibration plate.

17. An apparatus as claimed in claim 1, further comprising a cooling system for cooling said vibration plate.

18. An apparatus as claimed in claim 2, further comprising a vacuum means for evacuating the inside of said case.

19. An apparatus for injecting biological substances or biologically active substances into a biological material, comprising:

a single sealed cylinder;

a vibration plate attached to one end of said cylinder;

a hammer bullet provided in said cylinder and initially positioned at the other end of said cylinder; and a driving means for moving said hammer bullet, wherein said driving means moves said hammer bullet into contact with said vibration plate and causes biological substances or biologically active substances retained on the face of said vibration plate opposite the face contacted by said hammer bullet to radiate from said vibration plate.

20. An apparatus as claimed in claim 19, further comprising a case for mounting said cylinder.

21. An apparatus as claimed in claim 19, further comprising at least one duct at each end of said cylinder for discharging from the cylinder any excess fluid remaining after said hammer bullet strikes said vibration plate.

22. An apparatus as claimed in claim 21, further comprising vacuum means connecting to said ducts for evacuating said cylinder.

23. An apparatus as claimed in claim 19, wherein said compressed fluid source provides an impact pressure to said hammer bullet of about 1 to 30 $kg/cm^2$.

24. An apparatus as claimed in claim 19, further comprising a stopper positioned at the same end of said cylinder as said vibration plate for stopping said hammer bullet at a predetermined position.

25. An apparatus as claimed in claim 19, wherein said vibration plate is substantially flat and the face of said hammer bullet opposite to said vibration plate is formed to fit with the flat face of said vibration plate.

26. As apparatus as claimed in claim 19, wherein said vibration plate comprises a titanium alloy.

27. An apparatus as claimed in claim 19, wherein said vibration plate is comprises a layer of titanium alloy and a layer of magnetic material.

28. An apparatus as claimed in claim 19, wherein said vibrating material comprises an elastic resin.

29. An apparatus as claimed in claim 19, wherein the face of said vibration plate that retains the biological substances or biologically active substances is honed.

30. An apparatus as claimed in claim 19, wherein the face of said vibration plate that retains the biological substances or biologically active substances is ion spattered.

31. An apparatus as claimed in claim 19, wherein said hammer bullet comprises a material having a large specific gravity.

32. An apparatus as claimed in claim 31, wherein said hammer bullet comprises a material selected from lead, iron or depleted uranium.

33. An apparatus as claimed in claim 19, further comprising a noise-absorbing means at the same end of said cylinder as said vibration plate.

34. An apparatus as claimed in claim 19, further comprising a cooling system for cooling said vibration plate.

35. An apparatus as claimed in claim 20, further comprising a vacuum means for evacuating the inside of said case.

36. An apparatus as claimed in claim 1, wherein said vibration plate is convex along the direction of radiation of said biological substances.

37. An apparatus as claimed in claim 36, wherein said hammer bullet is convex alone the direction of radiation of said biological substances.

38. An apparatus as claimed in claim 1, wherein said vibration plate is concave along the direction of radiation of said biological substances.

39. An apparatus as claimed in claim 38, wherein said hammer bullet is convex along the direction of radiation of said biological substances.

40. An apparatus as claimed in claim 39, wherein said vibration plate has a protrusion on said face of said vibration plate opposite the face contacted by said hammer bullet.

41. An apparatus as claimed in claim 1, further comprising a first cap hingedly attached to one end of said cylinder and a second cap hingedly attached to the other end of said cylinder.

42. An apparatus as claimed in claim 19, further comprising a first cap hingedly attached to one end of said cylinder and a second cap hingedly attached to the other end of said cylinder.

43. An apparatus as claimed in claim 1, further comprising a sealing ring fitted about the periphery of said hammer bullet.

44. An apparatus as claimed in claim 19, further comprising a sealing ring fitted about the periphery of said hammer bullet.

45. An apparatus as claimed in claim 1, further comprising means for maintaining the working pressure at atmospheric pressure.

46. An apparatus as claimed in claim 19 further comprising means for maintaining the working pressure at atmospheric pressure.

* * * * *